(12) United States Patent
Zhu et al.

(10) Patent No.: US 10,627,344 B2
(45) Date of Patent: Apr. 21, 2020

(54) SPECTRAL ANALYSIS THROUGH MODEL SWITCHING

(71) Applicant: JP3 Measurement, LLC, Austin, TX (US)

(72) Inventors: Jie Zhu, Katy, TX (US); William Howard, Austin, TX (US); Randy Bishop, Holly Springs, NC (US)

(73) Assignee: JP3 Measurement, LLC, Austin, TX (US)

( * ) Notice: Subject to any disclaimer, the term of this patent is extended or adjusted under 35 U.S.C. 154(b) by 276 days.

(21) Appl. No.: 15/090,189

(22) Filed: Apr. 4, 2016

(65) Prior Publication Data
US 2016/0290919 A1    Oct. 6, 2016

Related U.S. Application Data

(60) Provisional application No. 62/142,253, filed on Apr. 2, 2015.

(51) Int. Cl.
*G01F 17/00* (2006.01)
*G01N 21/359* (2014.01)
(Continued)

(52) U.S. Cl.
CPC ......... *G01N 21/359* (2013.01); *G01N 33/225* (2013.01); *G01N 33/28* (2013.01);
(Continued)

(58) Field of Classification Search
CPC ...... G01N 21/31; G01N 21/359; G01N 33/22; G01N 33/225; G01N 33/28; G06F 17/3025; G06F 17/30528
(Continued)

(56) References Cited

U.S. PATENT DOCUMENTS 5,504,331 A * 4/1996 Lane ................... G01N 21/359
                                                    250/339.04
5,668,374 A    9/1997 DiFoggio et al.
(Continued)

FOREIGN PATENT DOCUMENTS

CA        2728505 A1    12/2009
CN     102841070 B       3/2015
(Continued)

OTHER PUBLICATIONS

International Search Report and Written Opinion dated Jul. 12, 2016 in corresponding International Patent Application No. PCT/US2016/025881.
(Continued)

*Primary Examiner* — Brook Kebede
(74) *Attorney, Agent, or Firm* — DuBois, Bryant & Campbell, LLP; William D. Wiese

(57) ABSTRACT

An improved method and system for analyzing multistate fluids using NIR spectroscopy. If the sample to be tested resides in a single state condition, the configuration file used in spectroscopic analysis will only be applied against a single model. However, if the sample to be tested is in a multi-state environment, an algorithm determines which model set of a plurality of model sets should be utilized based on the sample characteristics, and the configuration file used in spectroscopic analysis will be applied against the selected model. Results are generated showing the designated parameters.

18 Claims, 5 Drawing Sheets

(51) Int. Cl.
  *G06F 16/583* (2019.01)
  *G06F 16/2457* (2019.01)
  *G01N 33/22* (2006.01)
  *G01N 33/28* (2006.01)

(52) U.S. Cl.
  CPC .... *G06F 16/24575* (2019.01); *G06F 16/5838* (2019.01); *G01N 2201/10* (2013.01); *G01N 2201/12* (2013.01); *G01N 2201/129* (2013.01); *G01N 2201/13* (2013.01)

(58) Field of Classification Search
  USPC .................................................... 702/28, 50
  See application file for complete search history.

(56) References Cited

U.S. PATENT DOCUMENTS

| | | | |
|---|---|---|---|
| 8,645,082 | B2 | 2/2014 | Tan et al. |
| 8,686,364 | B1 | 4/2014 | Little, III |
| 2001/0033373 | A1 | 10/2001 | Sakai |
| 2009/0001262 | A1* | 1/2009 | Visser ................. G06K 9/6242 250/282 |
| 2010/0211329 | A1 | 8/2010 | Farquharson |
| 2017/0023538 | A1* | 1/2017 | Mertens ................. G01N 33/22 |

FOREIGN PATENT DOCUMENTS

| | | |
|---|---|---|
| EP | 2607885 A2 | 6/2013 |
| JP | 2005-227120 A | 8/2005 |
| WO | 2011-100435 A2 | 8/2011 |

OTHER PUBLICATIONS

Lida Esteve Agelet & Charles R Hurburgh, Jr., A Tutorial on Near Infrared Spectroscopy and Its Calibration, Critical Reviews in Analytical Chemistry, Nov. 5, 2010, 246-260, 40-4, Taylor & Francis, US.

* cited by examiner

SPECTRAL ANALYSIS THROUGH MODEL SWITCHING

PRIORITY STATEMENT UNDER 35 U.S.C. § 119 & 37 C.F.R. § 1.78

This non-provisional application claims priority based upon prior U.S. Provisional Patent Application Ser. No. 62/142,253 filed Apr. 2, 2015 in the names of Jie Zhu, William Howard, and Randy Bishop, entitled "Methods for Model Switching and Automatic Model Building," the disclosure of which is incorporated herein in its entirety by reference as if fully set forth herein.

BACKGROUND

Near-infrared (NIR) spectroscopy is a nondestructive method that provides simple, fast multiconstituent analysis on virtually any fluid and, although NIR spectroscopy is a secondary analytical method because the calibration and validation of measured NIR spectral data is correlated through statistical methods to reference data, it provides levels of accuracy and precision that are nearly comparable to primary reference methods. NIR test samples require no preparation or pretreatment with hazardous chemicals, solvents, or reagents, and the resulting NIR spectra contain a wealth of chemical and physical information on the sample and its constituents.

The processing of NIR absorption spectra, however, is often quite complex because the spectra often include broad overlapping NIR absorption bands that require special mathematical procedures for data analysis. In practice, NIR identification is performed by comparing a sample spectrum to a reference spectra of known materials, and mathematical models and so-called multivariate data analysis, or chemometrics, are used for NIR quantification.

In a laboratory, it may be practical to create new calibration models for each analyte tested or to have a library of models that can be accessed and substituted as necessary during testing depending on the process conditions for the specific sample being tested. In many practical applications, however, testing occurs in an environment in which the process conditions are fluctuating greatly. This is particularly true in instances in which measurements are being taken in real-time and the operator has no ability to standardize conditions, separate samples, or otherwise control the conditions under which the samples being tested are presented.

For example, the changing oil and gas market has increased the need for accurate, reliable hydrocarbon analysis. At the same time, the increase in the use of road and rail to transport crude and concentrate has strained the existing terminal loading infra-structure, resulting in the need to quickly analyze products delivered from different trucks or rail cards, each of which may be delivering hydrocarbon fluids under vastly different conditions. NIR spectroscopy is a very useful tool for measuring the properties of these fluids in-line, at pressure, with no sampling required. However, because the test conditions change frequently, the reference analytical models used in the NIR spectroscopy process are necessarily broad. As a result, the accuracy of the results obtained from such testing is reduced.

There is a need, therefore, for a method and system configured to easily test the composition of fluids using NIR spectroscopy under circumstances in which the process conditions are fluctuating.

SUMMARY

A method and system are provided for easily determining the composition of multi-state fluids by switching between readily available models during the NIR spectroscopy process. A process determines whether the sample to be tested is in a single state condition or a multi-state condition. If the process determines that the sample is in a single state condition, then the configuration file will only be applied against a single model during spectroscopic processing. Conversely, if the process determines that the sample is in a multi-state condition, then the configuration file will allow the use of different model sets under different conditions. In certain embodiments, an algorithm will be employed to determine which model set should be utilized based on the sample characteristics. The measured spectra is then compared against the selected model set and the results are then generated for the designated parameters.

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Figure 1:
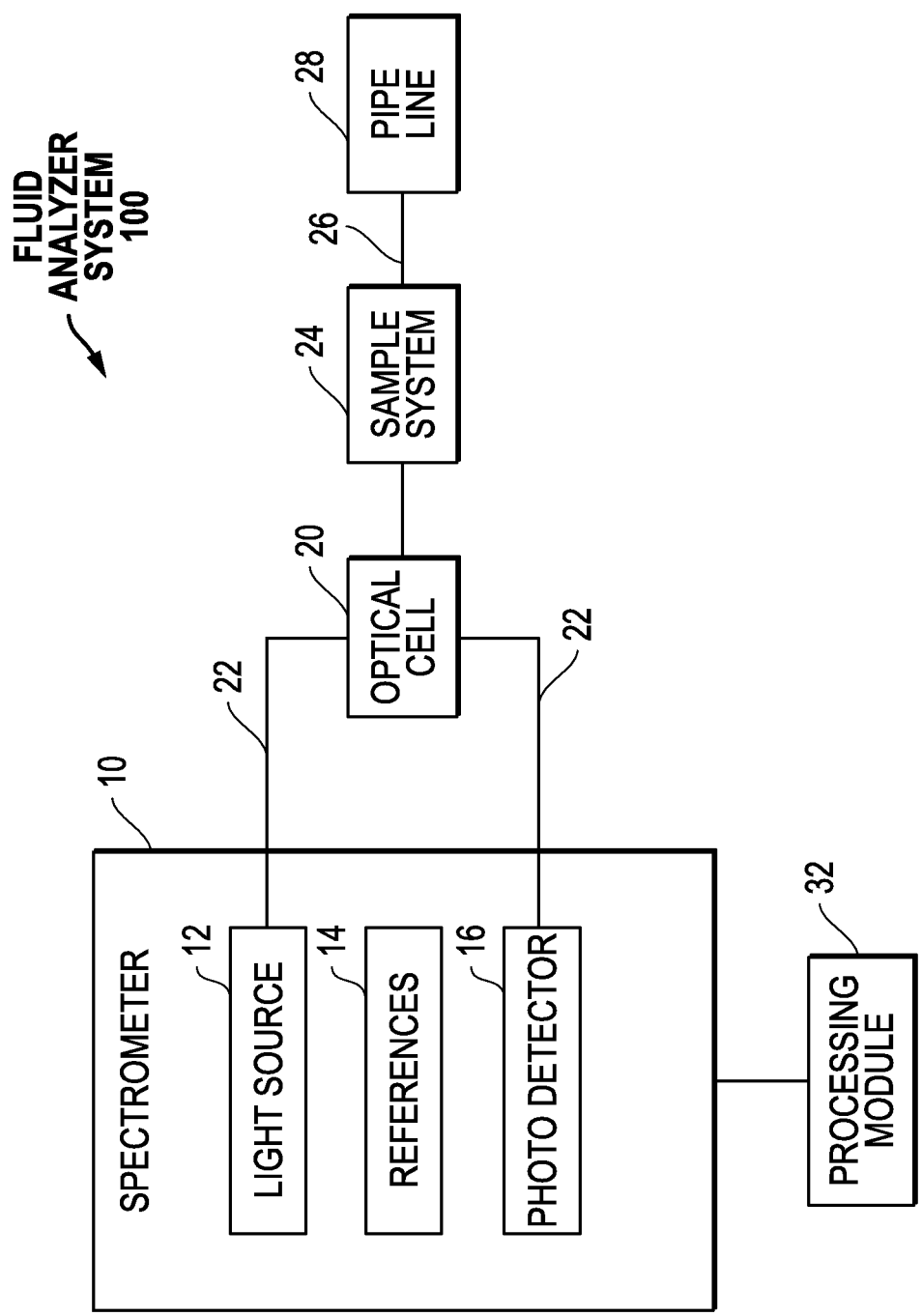
FIG. 1 shows a block diagram of a spectrometer operable to perform spectrographic analysis of fluids in the field.

The present invention is directed to improved methods and systems for, among other things, NIR spectral analysis utilizing model switching. The configuration and use of the presently preferred embodiments are discussed in detail below. It should be appreciated, however, that the present invention provides many applicable inventive concepts that can be embodied in a wide variety of contexts other than NIR spectral analysis of hydrocarbons. Accordingly, the specific embodiments discussed are merely illustrative of specific ways to make and use the invention, and do not limit the scope of the invention. In addition, the following terms shall have the associated meaning when used herein:

At any point at which fluids are measured, the fluid can be classified as being in a single state or in multiple states. A single state system indicates that the process nominally runs at only one process condition and, consequently, the values of any modeled parameter would be expected to be relatively flat within the process limits. However, in a multiple state environment, the process conditions are fluctuating between two or more states. For example, in the example cited earlier, during truck offloading operations, there might be N different types of trucks. As a result, the state of the value of a parameter being analyzed might have a corresponding N different nominal values.

NIR spectroscopy has been shown to be useful in determining the composition and properties of fluids in a single state. However, NIR absorption spectra are often complex and, as mentioned previously, normally possess broad overlapping NIR absorption bands. Moreover, chemical, physical, and structural properties of all species present in a sample influence the measured spectra and small sample-to-sample differences of a sample series can cause very small spectral differences. The measured NIR spectra is therefore multivariate and, even in a single state environment, requires substantial processing to decipher the results.

Although unique NIR absorption bands can normally be identified in the spectra of samples that are consistent with pure component spectra, interfering absorption bands due to other components and matrix variations can affect the spectroscopic measurements. Chemometrics uses mathematical and statistical procedures for multivariate data analysis to filter information that correlates to a certain property from a very large amount of data. In qualitative and quantitative NIR analysis, the relevant part from the multivariate NIR spectral data is extracted without losing important information while eliminating noise.

A multivariate calibration model describes the relationship between the dependent and independent parameters. The independent variables are the absorbances at a number of wavelengths and more than one dependent variable (concentration values) can be accounted for. The models can use one or more of the following elements: (i) principal components analysis (PCA) and partial least squares (PLS) regression to uncover optimal modeling strategies and to detect potential outliers in the calibration data set; (ii) if any sample or spectral variables are detected in the calibration data, exclude them from being used to build the models; (iii) use of partial least squares (PLS) regression to construct predictive calibration models from the calibration data generating a series of regression coefficients which, when multiplied with the absorbance values of an unknown gas sample's spectrum, yield the property of interest; (iv) use of genetic algorithms (GA) to select subsets of the spectral response variables to use in the predictive models to make the PLS models more robust with respect to known interfering effects in the spectra; and/or (v) use of PCA to generate an "outlier model" which can be run on-line to assess whether a field-collected spectrum is abnormal with respect to the spectra that were used to develop the models.

In quantitative NIR spectroscopy, empirical relationships are derived between the NIR spectra of a calibration set of samples and their corresponding reference analytical model for the constituents of interest. These NIR models are used to describe how the measured multivariate spectral features (e.g., absorption values of samples measured at many different wavelengths) are related to properties of the analytes. The more closely the model replicates the process conditions of the sample, the more accurate the results that are achieved. Now, through use of the embodiments of the present invention, it is possible to easily determine the composition of different fluids by switching between readily available models.

The need for testing samples under varying process conditions often occurs in the hydrocarbon processing industry. A representative embodiment of a fluid analyzer system 100 typically used in that industry is shown in FIG. 1. A spectrometer 10 known in the art includes a light source 12, integrated wavelength and amplitude references 14, and a photo detector 16. Spectrometer 10 is coupled to an optical cell 20 via fiber optic cables 22. A sample system 24 will extract gas 26 from a pipe line 28, whether in situ or as a bypass configuration, measure the pressure and temperature of the gas, direct the gas through optical cell 20 where it will be exposed to light from the scanning source 12, and reintroduce the sample back into the transmission line 28 or exhaust it to atmosphere. The spectral data will be transmitted back to the photo detector 16 via the fiber optic cables 22. The detector may, for example, be an Indium Gallium Arsenide (InGaAs) photo detector. The processing module 32 will process the spectrographic data and other measured fluid properties such as temperature and pressure, using various models and computational techniques to determine the chemical composition of the gas. Other properties of the gas such as hydrocarbon dew point, specific gravity and compressibility, may also be computed from the information collected. The results will then be stored for a later transmission and analysis, sent directly to a data gathering location, or both.

The processing module 32 may be a single processing device or a plurality of processing devices. Note that when the processing module 32 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The processing module 32 executes operational instructions corresponding to at least some of the steps and/or functions illustrated in FIG. 2.

Figure 2:
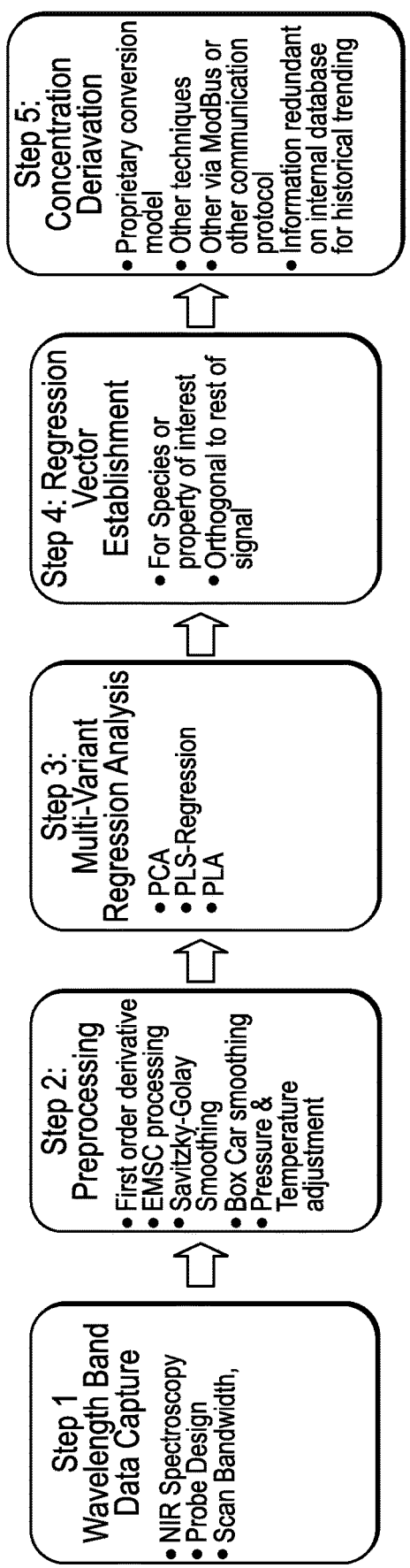
FIG. 2 provides a process flow diagram.

FIG. 2 provides a process flow diagram for a method to optically determine the properties of a fluid using, for example, fluid analyzer system 100. In Step 1, the raw data is collected using a NIR spectroscopy system and an optical cell in a fluid transportation system. This raw data collected from Step 1 is then sent to Step 2, preprocessing, where the data is processed and manipulated using certain algorithms such as taking the first order derivative, EMSC processing, Savitzky-Golay smoothing, box car smoothing, and/or pressure & temperature adjustment. This preprocessed data is then sent to Step 3, wherein a multivariate regression analysis, such as one of those described above, is performed on the data, followed by the regression vector establishment in Step 4. All of this processed data is then provided to the proprietary concentration derivation models in Step 5, yielding the desired output values for the fluid stream of interest.

As previously discussed, the process of converting the raw spectroscopic data via the processing module 32 may then involve dividing the first derivative spectrum by the pressure (in psi) for normalization. One or more calibration models may then be applied to the normalized first derivative spectrum to calculate energy content and contaminant concentrations. It is then possible to employ multivariate empirical modeling methods to develop various calibration models.

Figure 3:
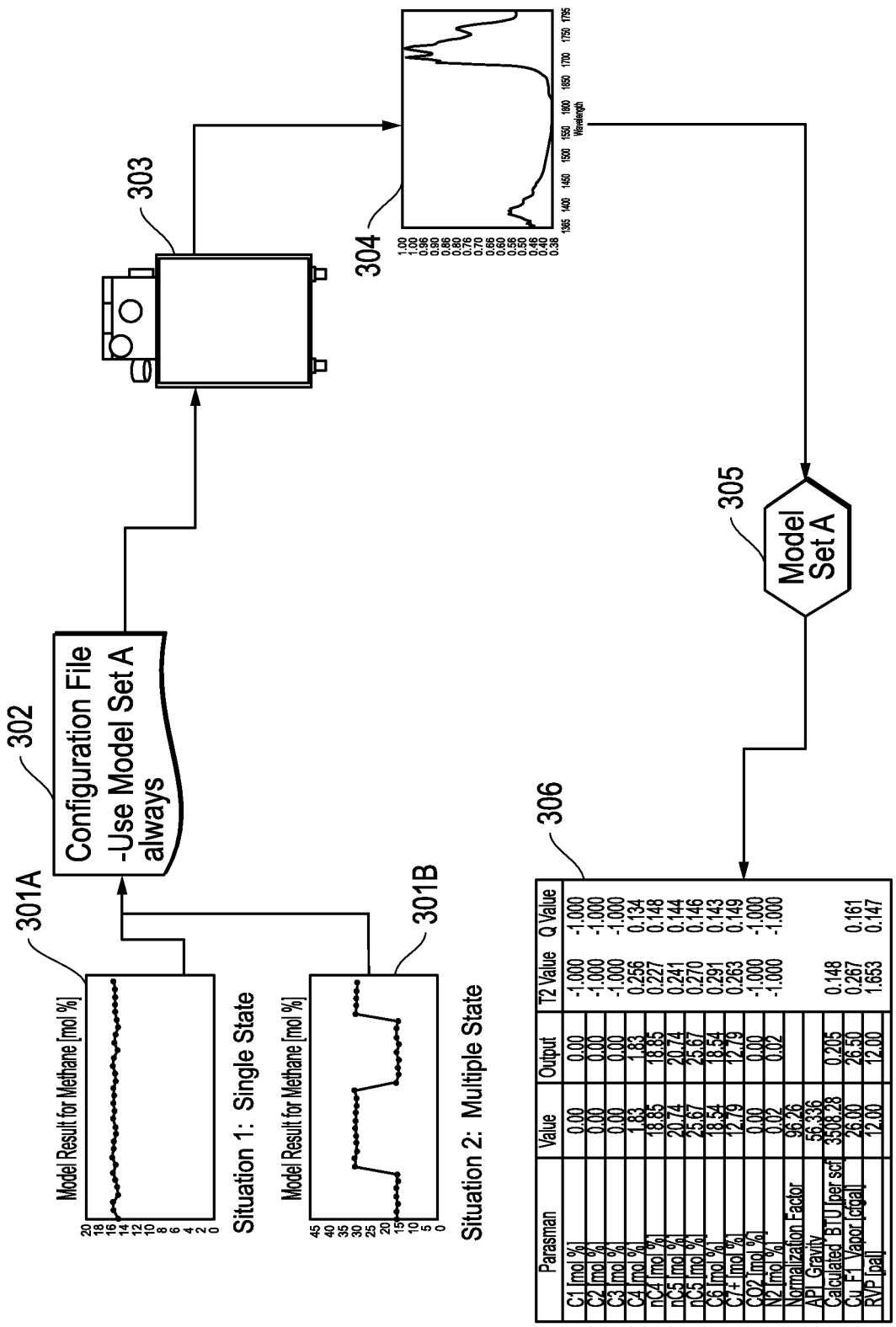
FIG. 3 shows a flow diagram of an NIR spectroscopic process known in the art.

Referring now to FIG. 3, which shows a flow diagram for a conventional method and system wherein only one model may be used at any time. Regardless of whether the analysis requires only a single state NIR spectral analysis 301A or a multi-state analysis 301B, the single state analysis must be used. The single model set is specified in the configuration file 302 and the model set and the configuration file 302 are prepared for testing in the spectrometer 303. A spectra 304 is generated by the spectrometer 303. The spectra 304 may be preprocessed as described above if desired, and then compared against model set A 305. The results 306 are then generated with the designated parameters.

When a single model is used, such as in the example shown above, the accuracy of the results is limited by the relevancy of the model to the sample being tested. By contrast, embodiments of the present invention allow the model to be switched or updated "on the fly" so that the model being employed bears greater relevance to the sample being tested. This type of model switching improves the accuracy of the results by allowing multiple models, each of which is constructed to be for a more specific case, as opposed to a single model that must necessarily be more general to handle multiple cases.

Figure 4:
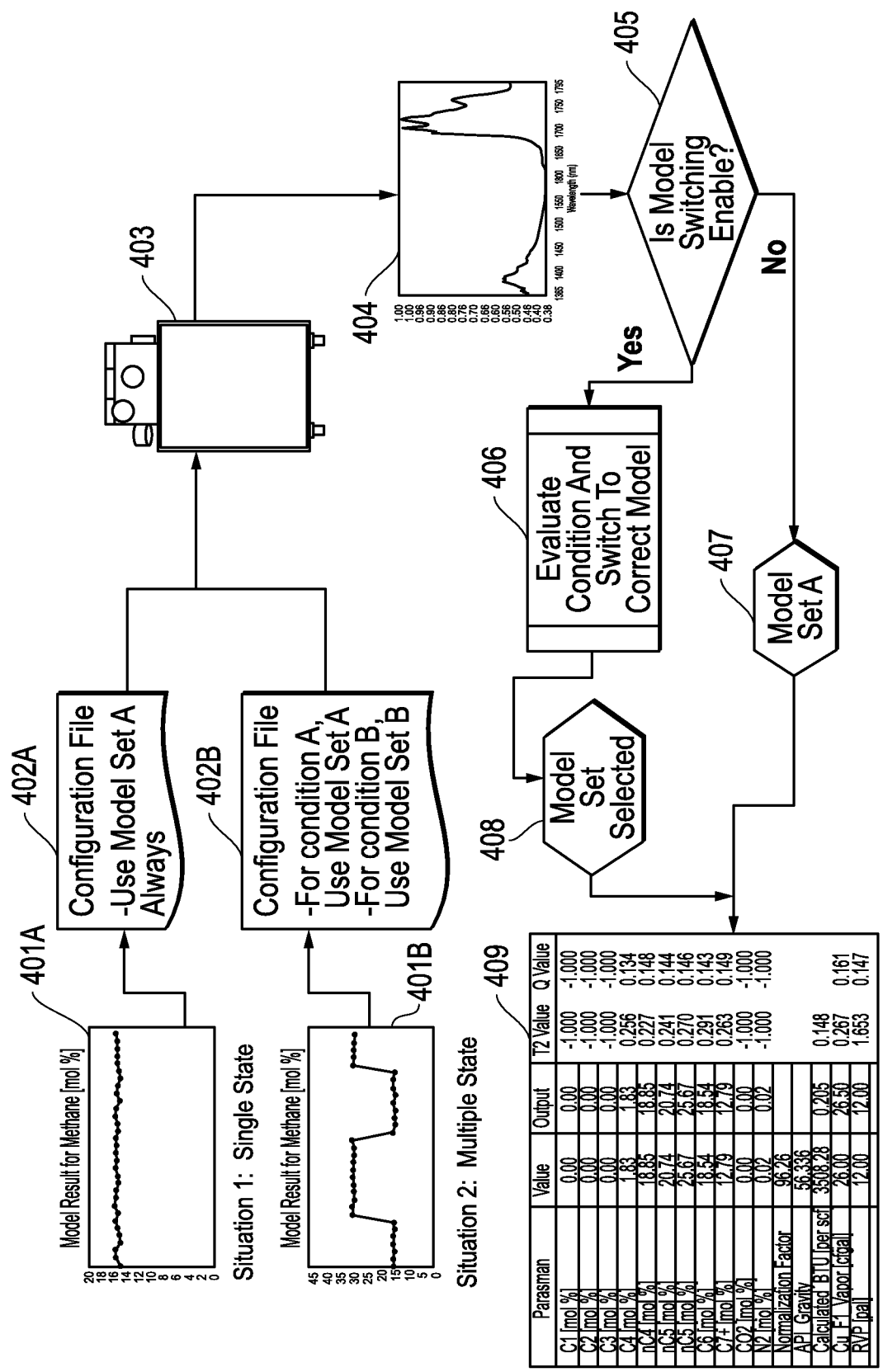
FIG. 4 shows a flow diagram depicting one embodiment of the NIR spectroscopic process employing model switching.

Referring now to FIG. 4, which shows a flow diagram of one embodiment of a method and system of the present invention wherein a plurality of models may be used. Initially, a manual and/or automated process will determine whether the measurement point represents a single state condition 401A or a multiple state condition 401B. If the process determines that measurement point is a single state condition 401A, then the configuration file 402A will allow for the application of only one model. On the other hand, if the process determines that the measurement point represents a multiple state condition 401B, then the configuration file 402B will allow the use of different model sets under different conditions. Either the model set from configuration file 402A or configuration file 402B are prepared for testing in the spectrometer 403. A spectra 404 is generated by the spectrometer 403. Once again, the spectra 404 may be preprocessed as described above if desired. If the original process detected a single state condition 401A, the spectra 404 is compared against model set A 407 and the results 409 are then generated showing the designated parameters. However, if the original process detected a multiple state condition 401B, an algorithm 406 will be employed to determine which model set should be utilized. The spectra 404 is compared against the selected model set 408 and the results 409 are then generated showing the designated parameters.

Figure 5:
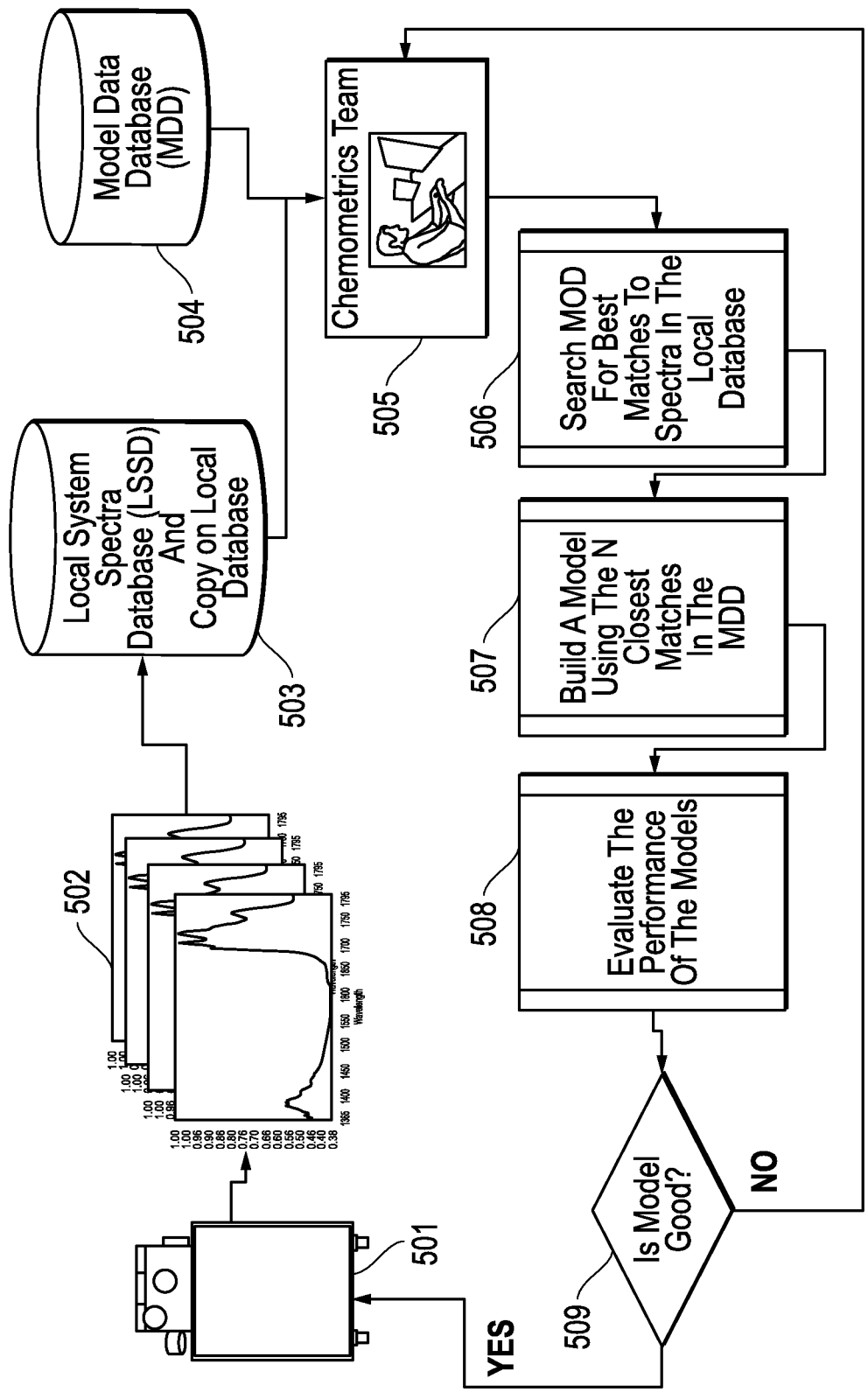
FIG. 5 shows a flow diagram depicting one embodiment of the NIR spectroscopic process employing automatic model building.

It will be apparent to those skilled in the art that calibration models may be developed manually through the methods described above. However, another embodiment of the present invention allows models to be built automatically. Referring now to FIG. 5, wherein a spectrometer 501 is installed in the field and the process is allowed to stabilize. After stabilization, fluid samples are scanned 502 and the digitized results are stored in a local system spectra database 503. In some embodiments, a copy of the spectra is downloaded on a nearly continuous basis to a local database.

When it is determined that a model is to be built, such as by the chemometrics team 505, a three step process is initiated. First, the model data database is searched 506 for spectra that most closely match the spectra from the spectrometer 501. Second, using the N most closely matched spectra, a model is built 507 for the spectrometer 501. It should be recognized that the variable N can be any desired number but for example, may be between 40 and 50. Finally, the performance of the model is evaluated 508 using a series of tests. If the model is accurate 509, the model is loaded onto the spectrometer 501 and is used to analyze ne fluid samples. On the other hand, if the model does not perform as expected, it is reviewed by the chemometrics team 505 who might create the model manually, request more samples, or change some parameters in the model-making process and repeat the automated process. The chemometrics team 505 need not be any specific group or person, but may be any method of evaluating and updating the model.

Those skilled in the art will appreciate the novelty and inherent value of automating the three steps described above so that they can be completed without human involvement.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for determining the amount of contaminants present in a fluid known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

What is claimed is:

1. A system for determining the composition of multi-state fluids, comprising:
   a first spectrometer configured to scan a series of fluid samples to capture NIR spectral analyses to create a plurality of reference analytical models for use during spectral analysis;
   a non-transitory computer database containing a plurality of reference analytical models, wherein each of the plurality of reference analytical models is for use during spectral analysis for a unique set of process conditions;
   a second spectrometer configured to scan a fluid sample in-situ, in real time;
   wherein, if the process conditions are a single state condition, using a single reference analytical model for spectral analysis; and if the process conditions are a multiple state condition, using the reference analytical model selected from the database that best corresponds to the process conditions for spectral analysis.

2. The fluid analyzer system of claim 1, wherein the determination of process conditions is repeated for each new fluid sample to be scanned.

3. The fluid analyzer system of claim 1, wherein the process conditions are temperature and pressure.

4. The fluid analyzer system of claim 1, wherein the reference analytical model comprises a calibration model corresponding to a specified set of process conditions.

5. The fluid analyzer system of claim 1, wherein the fluid samples are hydrocarbon liquids.

6. The fluid analyzer system of claim 1, wherein the fluid samples are liquefied natural gases.

7. The fluid analyzer system of claim 1, wherein the spectral analysis results in a report showing the constituent makeup of the fluid sample.

8. The fluid analyzer system of claim 1, wherein the spectral analysis results in a report showing the Reid vapor pressure of the fluid sample.

9. The fluid analyzer system of claim 1, wherein the first spectrometer and the second spectrometer are the same spectrometer.

10. A system for determining the composition of multi-state fluids, comprising:
   a first spectrometer configured to scan a series of fluid samples to capture NIR spectral analyses;
   a reference analytical model for use during spectral analysis, wherein the reference analytical model was created from the NIR spectral analyses;
   a non-transitory computer database containing a plurality of reference analytical models applicable to unique process conditions for use during spectral analysis;
   a fluid sample, wherein the fluid sample is scanned in-situ, in real time using a second NIR spectrometer and, if the process conditions of the fluid sample are in a single state condition, using a single analytical model for spectral analysis and, if the process conditions of the fluid sample are in a multiple state condition, determining which reference analytical model in the database best corresponds to the process conditions of the fluid sample and using the reference analytical model selected from the database for spectral analysis.

11. The system for determining the composition of multi-state fluids of claim 10, wherein the determination of process conditions of the fluid sample is repeated for each new fluid sample to be scanned.

12. The system for determining the composition of multi-state fluids of claim 10, wherein the process conditions are temperature and pressure.

13. The system for determining the composition of multi-state fluids of claim 10, wherein the reference analytical model comprises a calibration model corresponding to a specified set of process conditions.

14. The system for determining the composition of multi-state fluids of claim 10, wherein the fluid samples are hydrocarbon liquids.

15. The system for determining the composition of multi-state fluids of claim 10, wherein the fluid samples are liquefied natural gases.

16. The system for determining the composition of multi-state fluids of claim 10, wherein the spectral analysis results in a report showing the constituent makeup of the fluid sample.

17. The system for determining the composition of multi-state fluids of claim 10, wherein the spectral analysis in a report showing the Reid vapor pressure of the fluid sample.

18. The system for determining the composition of multi-state fluids of claim 10, wherein the first spectrometer and the second spectrometer are the same spectrometer.

* * * * *